United States Patent [19]
Capetanopolous et al.

[11] Patent Number: 5,624,641
[45] Date of Patent: Apr. 29, 1997

[54] GAS SENSING ASSEMBLY

[75] Inventors: Constantine D. Capetanopolous, Dobbs Ferry; Patrick J. Iannotta, Bellmore, both of N.Y.; Bryan S. Hobbs, Chertsey; John R. Finbow, Southampton, both of United Kingdom

[73] Assignee: SEM Corporation, Westbury, N.Y.

[21] Appl. No.: 243,452

[22] Filed: May 16, 1994

[51] Int. Cl.⁶ .................................................. G01N 27/00
[52] U.S. Cl. ........................... 422/98; 73/31.05; 73/31.07; 204/432; 422/83
[58] Field of Search ............... 422/83, 98; 436/116–118, 436/119, 122; 73/23.2, 23.31, 31.05, 31.07; 204/153.14, 153.19, 409, 431, 432

[56] References Cited

U.S. PATENT DOCUMENTS

| | | | |
|---|---|---|---|
| 4,225,842 | 9/1980 | Schlesselman et al. | 422/98 |
| 4,633,704 | 1/1987 | Tantram et al. | 204/415 |
| 5,092,980 | 3/1992 | Maurer et al. | 204/415 |

Primary Examiner—James C. Housel
Assistant Examiner—Jan M. Ludlow
Attorney, Agent, or Firm—Lee, Mann, Smith, McWilliams, Sweeney & Ohlson

[57] ABSTRACT

A gas sensing assembly from which a number of gas sensing devices can be constructed for determining the concentration of an active gas in a gas mixture. The assembly comprises a self-contained sensing unit including a sensing element at which active gas reacts and is consumed, an output signal being produced proportional to the rate of reaction of active gas. A number of different control members are provided each defining a respective gas diffusion barrier, each member being separately securable to the sensing unit and detachable therefrom while leaving the sensing unit intact to enable gas sensing devices of different sensitivities to be constructed from the same sensing unit.

12 Claims, 4 Drawing Sheets

GAS SENSING ASSEMBLY

The invention relates to gas sensing assemblies from which a number of gas sensing devices can be constructed and methods of constructing gas sensing devices from such assemblies.

In the field of combustion source monitoring, it is becoming increasingly important to provide accurate but relatively inexpensive monitoring methods to ensure that combustion source emissions conform with national and international regulations. For example, the Environmental Protection Agency (EPA) in the USA has set out strict requirements which must be complied with by combustion sources. In the past, the standard monitoring methods have included chemiluminescence and infrared techniques but these are expensive and complex to use. This is a particular problem for small scale utilities.

Gas sensing devices for detecting the concentration of an active gas in a gas mixture are well known and include, for example, electrochemical sensors and pellistors. However, these have not been used previously in combustion source monitoring due to their susceptibility to moisture and the inability in commercial sensors of this type to satisfy some of the strict requirements laid down by the regulatory authorities. For example, the USA EPA requires that the "span" of a monitor shall be selected such that the pollutant gas concentration equivalent to the emission standard is not less than 30% of the span. The span is the upper limit of the gas concentration measurement range displayed on a data recorder. Thus, even with a sensor adapted to a particular gas, a range of such sensors would be necessary to cope with various gas concentrations in order to satisfy the span requirement.

U.S. Pat. No. 5,092,980 describes a system for varying the sensitivity of a sensor but this is complex in requiring the selective actuation of pistons to cover openings and does not result in a cost effective sensor.

In accordance with one aspect of the present invention, a gas sensing assembly from which a number of gas sensing devices can be constructed for determining the concentration of an active gas in a gas mixture comprises a self-contained sensing unit including a sensing element at which active gas reacts and is consumed, an output signal being produced proportional to the rate of reaction of active gas; and a number of different control members each defining a respective gas diffusion barrier, each member being separately securable to the sensing unit and detachable therefrom while leaving the sensing unit intact to enable gas sensing devices of different sensitivities to be constructed from the same sensing unit.

In accordance with a second aspect of the present invention, a method of constructing a gas sensing device of a desired sensitivity comprises selecting a suitable control member from the number of different control members of a gas sensing assembly according to the first aspect of the invention; and securing the selected control member to the self-contained sensing unit of the gas sensing assembly.

We have realised that by constructing gas sensing devices in two parts it is possible to provide a range of control members which can be selectively secured to the sensing unit in dependence upon the particular sensitivity requirement of the application concerned. The idea of a two part gas sensing device is disclosed in GB-A-2073430 but this does not recognise the suitability of such two part devices for achieving different sensitivities.

In general, there is a need to provide a range of gas sensing devices to enable different gases to be detected. A typical range of gases which would need to be detected include CO, $SO_2$, NO and $NO_2$. In the case of conventional single component units, these can be made easily identifiable as to the gas which they detect. However, when two part units are provided, such as in accordance with the first aspect of the invention, or in accordance with the disclosure in GB-A-2073430, there is a significant risk that a sensing unit for use with one gas is attached to a control member for use with a different gas leading to incorrect results.

We provide, therefore, in accordance with a third aspect of the invention, a gas sensing assembly from which a number of gas sensing devices can be constructed for determining the concentration of active gases in gas mixtures comprising a number of self-contained sensing units each including a sensing element at which a respective active gas reacts and is consumed, an output signal being produced proportional to the rate of reaction of the active gas; and a number of different control members, each defining a gas diffusion barrier and being adapted for use only with sensing units for sensing a corresponding one of the active gases, the control members having substantially the same shape, corresponding control members and sensing units having unique, cooperating locating arrangements so that a control member can only be fitted to a corresponding sensing unit, and wherein each control member is separately securable to the corresponding sensing unit and detachable therefrom while leaving the sensing unit intact.

With this aspect of the invention, there is no danger of control members being secured to the wrong sensing unit while the control members can be made in a substantially identical form which makes the assembly particularly attractive commercially.

Typically, the cooperating locating arrangements comprise cooperating pegs and sockets arranged in a unique manner. For example, pegs could be mounted on the sensing unit and sockets on the control members or vice versa or there could be a mixture of pegs and sockets on each of the sensing units and control members.

In the preferred assembly, a range of sensing units for different gases will be provided, each with a range of control members defining different sensitivities.

The sensing element can take a variety of forms such as a pellistor but preferably forms part of a galvanic electrochemical cell.

Typically, the gas diffusion barrier provided by the control members comprises a gas phase diffusion barrier or a Knudsen barrier. The gas phase diffusion barrier may be in the form of one or more capillaries.

Depending upon the gas to be sensed, a control member may also include a filter for removing active gases which are not to be sensed. Thus, in the case of a NO sensor, a filter is needed to remove $NO_2$ and $SO_2$.

Alternatively, an auxiliary control member containing a filter separate from the one control member and sensing device, could be provided.

Conveniently, the filter is positioned downstream of the gas diffusion barrier in a manner similar to that described in U.S. Pat. No. 4633704. Alternatively, the filter could be positioned upstream of the gas diffusion barrier.

The control members may be secured to the sensing units in a variety of ways but in the preferred arrangement, the assembly further includes common securement means for securing a combined sensing unit and control member together and to a support. In this way, a single set of securement means is required both for securing the sensing unit and control member together and for securing the combined assembly to a support. For example, the securement means may comprise a nut and bolt arrangement or the like. This makes it very simple for the user to attach gas sensing devices to the support without the need for any additional preliminary step of securing a control member to the sensing unit.

Typically, each of the control members is square in plan although other geometries are also possible.

BRIEF DESCRIPTION OF THE DRAWINGS

Some examples of gas sensing assemblies and methods according to the invention will now be described and contrasted with a known example with reference to the accompany drawings, in which:

A conventional electrochemical sensor will first be described with reference to FIG. 1. This is described in more detail in GB-A-2094005. Referring to FIG. 1, a sensing electrode 1 comprises a porous PTFE support tape to which is bonded a catalyst/PTFE mixture, the latter covering an area of smaller diameter than the tape. A counter electrode 2 is of similar construction but with a hole 3 through which a wick 4 passes to an electrolyte reservoir/expansion chamber 5. Strip-like current collectors 6, 7 contact the sensing and counter electrodes respectively (see also FIG. 2) and lead out to terminal posts 8 (one only shown). The wick 4 extends from a separator 9 which with a further separator 10 and an annular gasket 11, which gasket may conveniently be cut from porous PTFE tape, makes up an interior sandwich between the electrodes.

Figure 1:
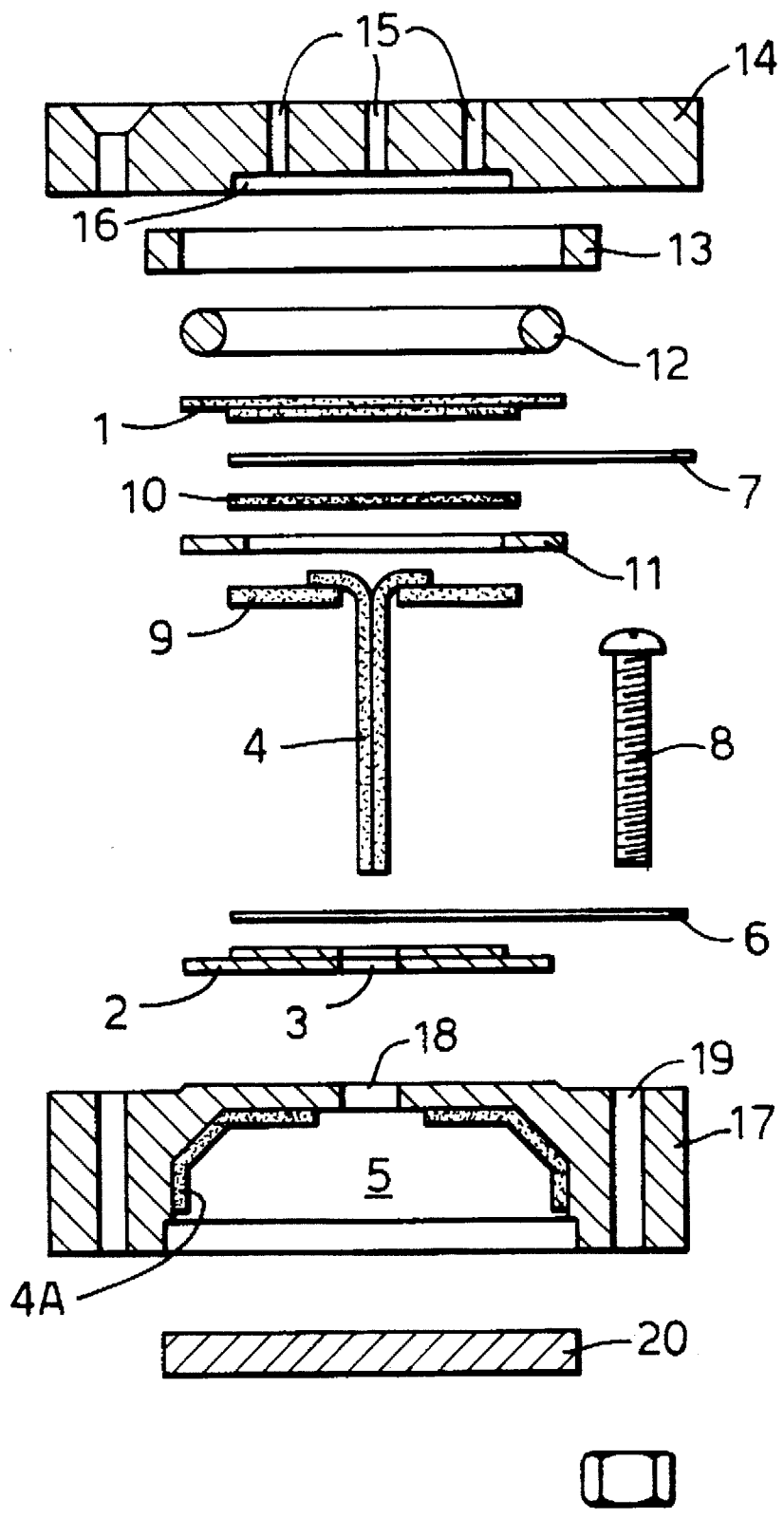
FIG. 1 is an exploded cross-section through a known electrochemical cell.

Above the sensing electrode 1 is an O-ring 12 with a rigid retaining ring 13 of smaller height than the O-ring, the underside of which has slots (not shown) to allow egress of the current collectors 6 and 7. A top plate 14 carries capillary holes 15 which form a diffusion barrier for restricting access of the gas to be detected and has a cavity 16 to allow for diffusion across the sensing electrode. A bottom plate 17 carries the electrolyte reservoir/expansion chamber 5, the wick 4 passing through a hole 18 therein, and arranged to make good contact with wick extension 4a which extends around the perimeter of chamber 5 to ensure contact with the electrolyte in all sensor attitudes.

After assembly, the whole is clamped together with bolts and nuts (not shown) through the top and bottom plates 14 and 17. The nuts and bolts are tightened sufficiently to suitably compress the O-ring. The outer annular portions of the PTFE tape in the electrodes 1 and 2, not covered with catalyst, are thus brought into intimate compressive contact with the PTFE gasket 11. The PTFE moulds around the current collectors leading out of the cell from the electrodes. Sealing of very high integrity is thus achieved because of the great resistance of hydrophobic porous PTFE to aqueous penetration. The height of the ring 13 is chosen, so that the desired degree of compression is obtained by simply bolting up tight to this. O-ring compressions of between 15% and 50% have been successfully employed.

With the assembly upside down, electrolyte may now be introduced to partially fill the reservoir 5 and the cover plate 20 is sealed in position in the plate 17. The electrolyte wets up the separators 9 and 10 via the wick 4 to form the electrolyte connection between the electrodes. The amount of electrolyte is chosen to only partially fill the reservoir/expansion chamber 5 and so that volume changes resulting from gain or loss of water vapour during the operation of the sensor may be accommodated.

In this case, a two electrode sensor is described. The invention is equally applicable to three electrode sensors.

It will be seen that this gas sensing device forms a complete unit and in particular if it was desired to remove the top plate 14, it would be necessary to disassemble the entire device with an associated loss of electrolyte and indeed in practice this is not possible.

Figure 2:
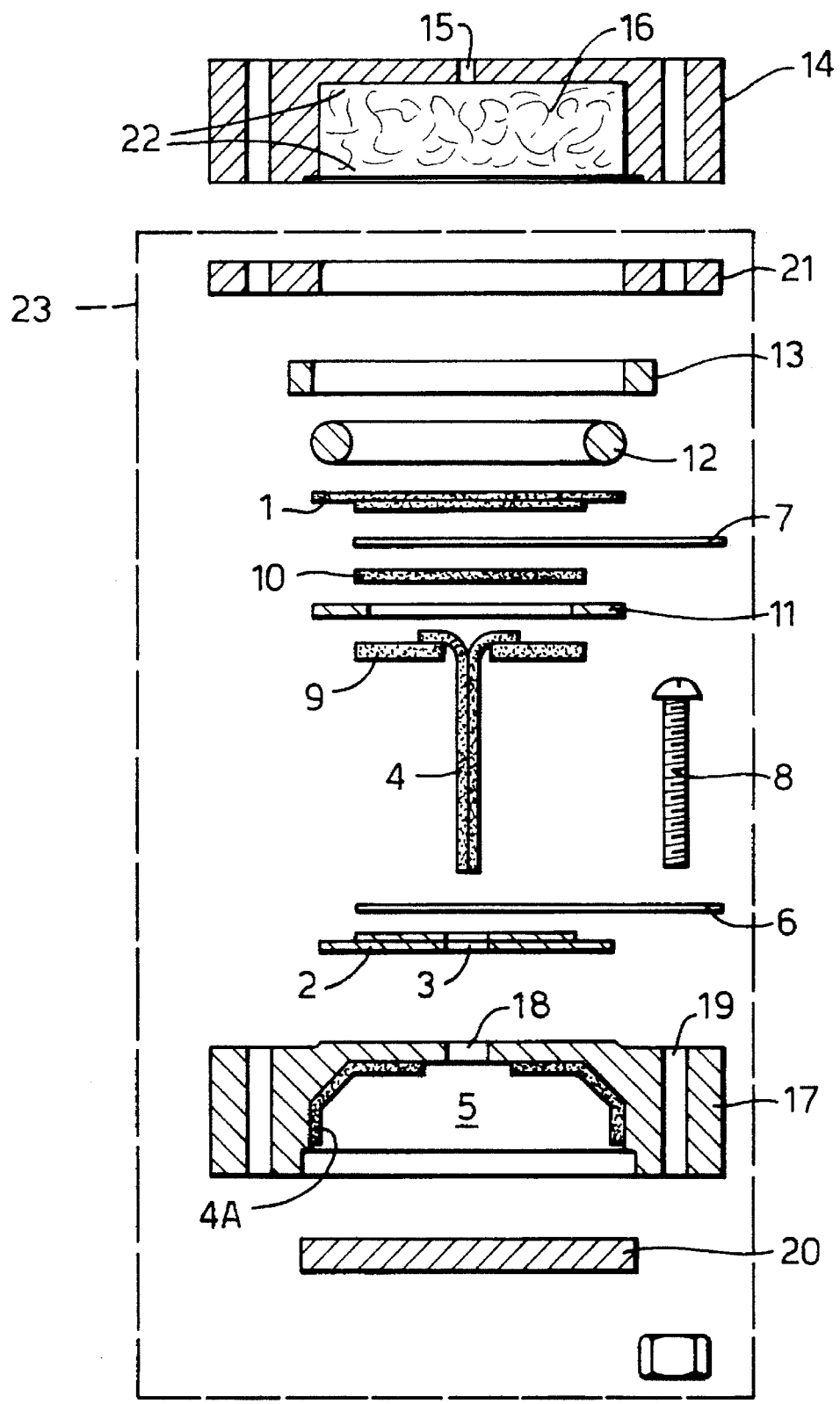
FIG. 2 is a view similar to FIG. 1 but showing the construction of a gas sensing device from an assembly in accordance with an example of the invention.

FIG. 2 illustrates an example of a device constructed from an assembly according to the invention. In FIG. 2, those items which are the same as in FIG. 1 have been given the same reference numerals and will not be described further. As can be seen, the main difference is that an additional adaptor plate 21 is interposed between the top plate 14 and the remainder of the device. The adaptor plate 21 is permanently fixed to the base plate 17 by bolts (not shown) or by bonding, ultrasonic-welding etc. so that the components within the dashed line 23 define the self-contained sensing unit. The top plate 14 has, in this case, a diffusion barrier 15 formed by a single capillary hole together with an inboard filter 16 to remove cross-interfering gases. The filter material is held in place by means of fixed porous PTFE tapes 22. The top plate 14 is fixed to the base plate 17 by bolts which extend through holes 19 and this will be described in more detail below.

For simplicity of comparison with FIG. 1, the base plate 17 in FIG. 2 has been shown as the same as FIG. 1. However, as will be explained below, particularly in connection with FIG. 3, the base plate may have a slightly different form.

Figure 3A:
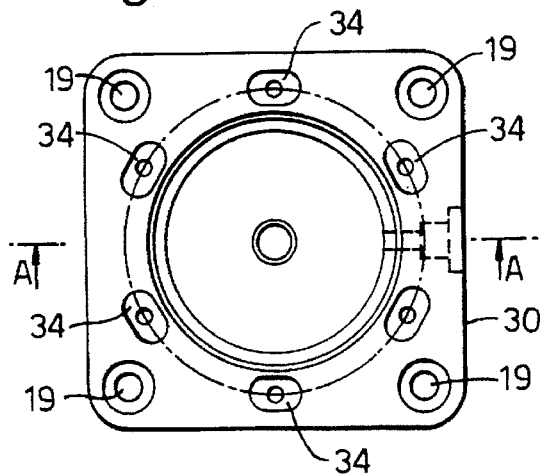
FIGS. 3A and 3B are a plan, and cross-section on the line A—A, respectively of a base plate of a sensing unit.
Figure 3B:
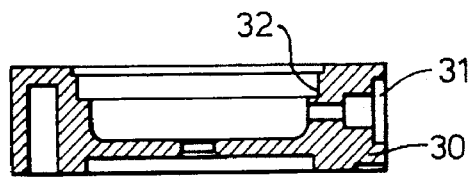

FIG. 3A illustrates a base plate 30 which, as can be seen, has a square shape in plan and with a side opening conduit 31 for injecting electrolyte. The central portion 32 of the base plate 30 is formed as a moulded-in electrode well which effectively replaces the retaining ring 13 in FIG. 1.

Figure 4A:
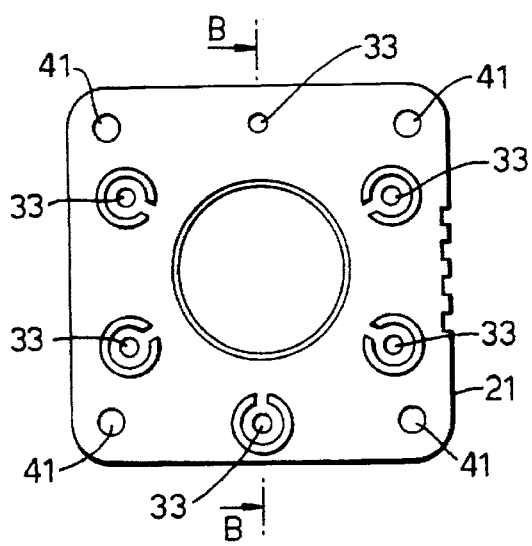
FIGS. 4A and 4B are an underneath plan, and cross-section on the line B—B, respectively of an adaptor plate for mounting to the base plate of FIG. 3.
Figure 4B:
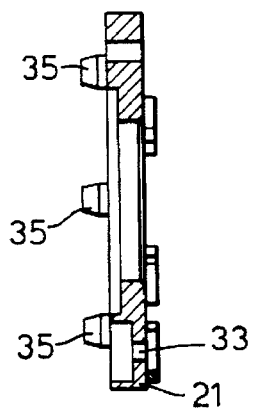

FIGS. 4A and 4B illustrate the adaptor plate 21 in more detail. Again, this has a square shape in plan so as to conform with the square shape of the base plate 30. The adaptor plate 21 is secured to the base plate 30 by bolts (not shown) extending through apertures 33 in the adaptor plate 21 and apertures 34 in the base plate 30.

As can be seen more clearly in FIG. 4B, the upper face of the adaptor plate 21 has a set of upstanding spigots or pegs 35 whose purpose will be described in more detail below.

Figure 5A:
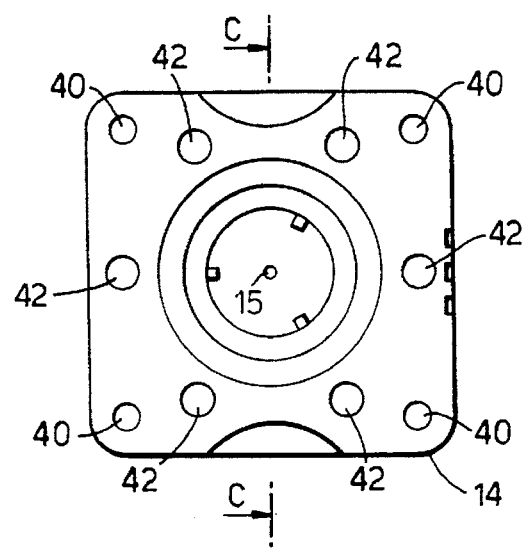
FIGS. 5A and 5B are an underneath plan, and cross-section on the line C—C, respectively of a first example of a top plate.
Figure 5B:
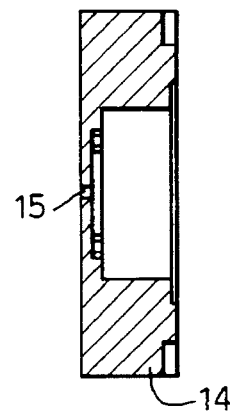

FIGS. 5A and 5B illustrate a first example of a top plate 14 similar to the top plate 14 shown in FIG. 2. As can be seen in FIG. 5A, the under surface of the top plate 14 has a set of holes 40 which align with holes 41 in the adaptor plate 21 and holes 19 in the base plate 30. In addition, a set of six substantially equally angularly spaced location hole positions 42 are provided. As can be seen in FIG. 5A, these are labelled 1–6 respectively. In practice, not all of the hole positions 42 will be drilled but a particular combination of these holes which is unique to the type of sensor to which the top plate is to be attached. In the same way, the top face of the adaptor plate 21 will be formed with a corresponding set of spigots 35 arranged in a unique fashion. Table 1 below illustrates an example of the hole positions 42 which will be drilled for each of three sensor types.

TABLE 1

| Sensor Type | Hole Position | | | | | |
|---|---|---|---|---|---|---|
|  | 1 | 2 | 3 | 4 | 5 | 6 |
| $SO_2$ | X |   | X |   | X |   |
| NO |   |   | X |   | X | X |
| CO | X | X |   |   |   | X |

X indicates hole position is drilled.

It will be noted that not only do these unique combinations of hole positions and spigots ensure that only one type of top plate can be fitted to one type of sensing unit, but the relative orientation between the two components is also unique.

FIG. 5B illustrates the internal construction of the top plate 14 of FIG. 5A and as can be seen this is adapted for use with a filter as is explained in more detail in connection with FIG. 2. In this case, the layers of PTFE 22 are not shown.

Figure 6A:
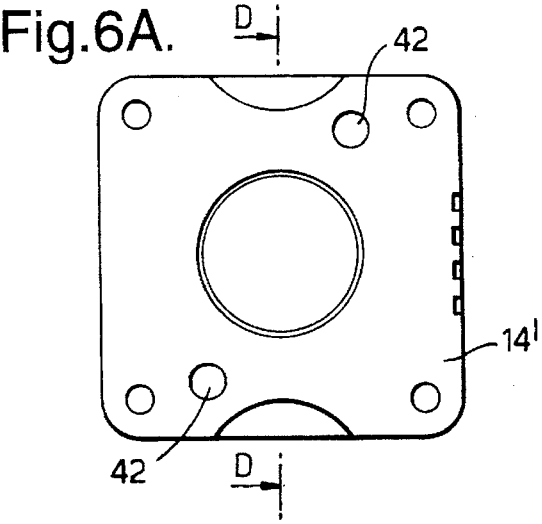
FIGS. 6A and 6B are an underneath plan, and cross-section on the line D—D, respectively of a second example of a top plate; and, FIG. 7 illustrates two sensing devices mounted to a combustion source monitor gas manifold.
Figure 6B:
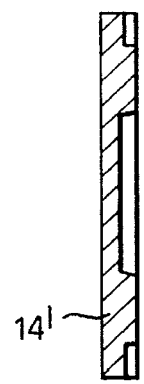

For $NO_2$ sensing, no filter is required and a suitable top plate 14' is shown in FIG. 6. The construction of this top plate 14' is similar to that shown in FIG. 5 except that no filter is required so that the top plate is much thinner as seen in FIG. 6B. In this case, two spigot receiving holes 42 only are drilled so as once again to define a unique arrangement for mounting to a corresponding sensing unit.

The spigot/hole arrangement ensures that only top plates of a suitable type can be mounted to corresponding sensing units. Typically, a range of different top plates with the same hole configuration will be constructed each having different gas phase barrier arrangements. Thus, in the examples shown in the drawings, a single capillary is used in each case. Other top plates may have a number of capillaries or even a porous structure so that the sensitivity of a particular sensing unit can be varied.

Figure 7:
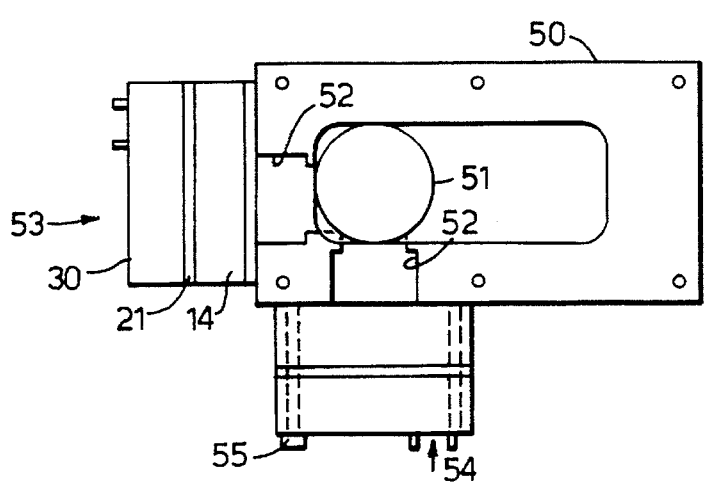

An important application of these sensors is in combustion source monitoring as described above. FIG. 7 illustrates a combustion source monitor gas manifold 50 for mounting about a gas conduit 51 through which a sample of the gas, which has been conditioned, is delivered. The manifold 50 has a pair of sampling tubes 52 which communicate with the conduit 51 and to each of which a respective sensor assembly 53, 54 according to examples of the invention are mounted. Each sensor assembly 53, 54 has a base plate 30, an adaptor plate 21, and a top plate 14, the plates being mounted and secured together and secured to the manifold 50 by the same set of bolts, one of which is shown in FIG. 7 at 55. Typically, the sensing devices 53, 54 will be adapted to sense different gases.

The choice of filter is made in dependence upon the gas to be sensed and to optimise performance of the sensor.

A typical combustion source monitor will comprise four gas sensing devices of the type described above for sensing CO, $SO_2$, NO, and $NO_2$, respectively together with a fifth gas sensing device for sensing $O_2$ for diagnostic purposes. The toxic gas sensing devices need to be regularly calibrated and a typical protocol to achieve this would be as follows:

1. Air Leak Check

The leakage of air (oxygen) into the monitor will cause the gas sensing devices to read incorrectly. Thus, the oxygen gas sensing device is used to monitor for the presence of oxygen during calibration of a NO sensing device since the calibration gas is $O_2$ free. If oxygen is detected, a message can be displayed on a monitor or printer such as:
SENSOR CALIBRATION FAILURE
SYSTEM DETECTED AN AIR LEAK 2. Sensor Selectivity Check In the next check, the output of each sensor is checked against a stored sensitivity value in a memory for that sensor. As described above, for example, in many applications it is important that the correct sensitivity is set in accordance with the "span" of the monitor. This also enables the operator to check that the correct control member (i.e. with the correct sensitivity) has been fitted. During calibration, the monitor is supplied with each of the gases to be sensed in sequence and the output from the corresponding sensor monitored. If the sensor output is within a predetermined acceptable limit then either no message will be output or possibly a message confirming acceptance. If it is outside this acceptable limit then a suitable message will be output indicating this.

Even if the output is within an acceptable limit, it may exceed a threshold limit and then a notification similar to the following might be output:
SENSOR CALIBRATION SUCCESSFUL
REPLACE SENSOR SOON OR CHECK CALIBRATION GAS If the sensor output is below a preset failure level then an output similar to the following would be issued:
SENSOR CALIBRATION LEVEL
REPLACE SENSOR OR CHECK SPAN GAS 3. Sensor Cell Selectivity Check During calibration, it is also important to check that there is no sensitivity of a sensor to one of the other gases or if there is that this is compensated for or that the relevant filter is replaced. Thus, while a calibration gas is being supplied, outputs of all the gas sensing devices is monitored and if any rises above some predetermined level, for example 2.5%, then the following warning could appear:
REPLACE XX SENSOR FILTER SOON If the cross sensitivity of the interfering gas increases further, perhaps to 5%, the following message could appear:
REPLACE XX SENSOR FILTER In the case of an $SO_2$ sensing device, it is not possible to filter out $NO_2$ as an interfering gas and so the $SO_2$ device is calibrated for $NO_2$ as a cross-interference and compensated electronically using the cross-interference calibration reading and the $NO_2$ sensing device reading.

This results in a quality assured product leading to a control member which may be termed a quality assured precision control module (QAPCM).

We claim:
1. A kit for the assembly of a plurality of gas sensing devices for determining the concentration of active gases in gas mixtures, the kit comprising a number of self-contained sensing units each including a sensing element at which a respective active gas reacts and is consumed, an output signal being produced proportional to the rate of reaction of the respective active gas; and a number of different control members, each defining a gas diffusion barrier and being adapted for use only with sensing units for sensing a corresponding one of the active gases, the control members having substantially the same shape, corresponding control members and sensing units having unique, cooperating locating arrangements so that a control member can only be fitted to a corresponding sensing unit to form a respective one of said gas sensing devices, and wherein each control member is separately securable to the corresponding sensing unit and detachable therefrom while leaving the sensing unit intact.

2. A kit according to claim 1, wherein the cooperating locating arrangements comprise cooperating pegs and sockets.

3. A kit according to claim 2, wherein the pegs are provided on the sensing unit.

4. A kit according to claim 1, wherein at least one sensing unit can be fitted to a plurality of said control members, said plurality of control members defining different gas diffusion barriers.

5. A kit according to claim 1, wherein at least one of the control members includes a filter.

6. A according to claim 5, wherein, when said control member is secured to said corresponding sensing unit, said filter is positioned between said sensing unit and said diffusion barrier.

7. A kit according to claim 1, wherein the gas diffusion barrier comprises a gas phase diffusion barrier or a Knudsen barrier.

8. A kit according to claim 7, wherein the gas phase diffusion barrier comprises one or more capillaries.

9. A kit according to claim 4, wherein the different control members have different numbers of capillaries.

10. A kit according to claim 1, further including common securement means for securing a sensing unit and control member together and to a support.

11. A kit according to claim 1, wherein the control members are substantially square in plan.

12. A kit according to claim 1, wherein the sensing unit comprises a galvanic electrochemical cell.

* * * * *